United States Patent [19]
Kooiman

[11] Patent Number: 5,895,217
[45] Date of Patent: Apr. 20, 1999

[54] HARD PALATE SUPPORTING DEVICE AND METHOD OF MAKING IT READY FOR FITTING

[75] Inventor: Johan Anton Kooiman, Reeuwijk, Netherlands

[73] Assignee: Orthoton B.V., Gouda, Netherlands

[21] Appl. No.: 08/922,467

[22] Filed: Sep. 3, 1997

[30] Foreign Application Priority Data

Aug. 7, 1997 [NL] Netherlands ............... 1006736

[51] Int. Cl.⁶ .................................. A61C 3/00
[52] U.S. Cl. .................. 433/7; 433/18; 433/21
[58] Field of Search ................. 433/6, 7, 18, 21

[56] References Cited

U.S. PATENT DOCUMENTS

| | | | |
|---|---|---|---|
| 1,582,570 | 4/1926 | Brust | 433/7 |
| 3,293,474 | 12/1966 | Denholtz | 433/21 |
| 4,272,240 | 6/1981 | Glassman | |
| 5,064,370 | 11/1991 | Jones | 433/18 X |
| 5,096,416 | 3/1992 | Hulsink | 433/6 |

FOREIGN PATENT DOCUMENTS

| | | | |
|---|---|---|---|
| 0 372 316 | 6/1990 | European Pat. Off. | |
| 785198 | 4/1934 | France | 433/7 |
| 981973 | 5/1943 | France | 433/7 |

OTHER PUBLICATIONS

P. Barwart et al., "Removable Nance Appliance," *The Journal of Clinical Orthodontics*, Aug. 1996, pp. 447–449.

*Primary Examiner*—Nicholas D. Lucchesi
*Attorney, Agent, or Firm*—Young & Thompson

[57] ABSTRACT

A hard palate supporting device for pushing apart or anchoring of upper teeth, such as molars and/or premolars, includes a hard palate supporting element and/or carrier therefor, a hinge by means of which the supporting element or carrier is rotatable relative to an axis of rotation extending in the transverse direction of the teeth, and a spring which on rotation of the supporting element or carrier in a direction away from the position resting against the hard palate exerts on the supporting element or carrier a force counter-acting such rotation. The supporting device can also include a stopper which limits rotation in the direction of the position resting against the hard palate, preferably to the contact position.

21 Claims, 1 Drawing Sheet

HARD PALATE SUPPORTING DEVICE AND METHOD OF MAKING IT READY FOR FITTING

BACKGROUND OF THE INVENTION

The present invention relates to a hard palate supporting device for distalizing or anchoring of upper teeth, such as molars and/or premolars, comprising a hard palate supporting element and/or carrier therefor.

Such a hard palate supporting device is known in orthodontics, where it is often referred to as a Nance appliance. The supporting element is also sometimes referred to as a Nance button.

In the case of the hard palate supporting devices known until now the supporting element is generally permanently fixed by cementing or is removably fixed to be removable by the orthodontist. Such a removable fixing by the orthodontist is described in, for example, The Journal of Clinical Orthodontics, Volume XXX, No. 8, of August 1996 by Paul Barwart and M. Richter. According to the article, this removable fixing is unsuitable for removal by the patient.

Supporting elements, also known as Nance buttons, both those permanently fixed and those fixed removably for the orthodontist, have the disadvantage that a dirt trap is formed underneath the supporting element, providing a place where bacteria can grow, and thus a place where the mucous membranes of the hard palate can become inflamed.

SUMMARY OF THE INVENTION

The object of the present invention is to provide a hard palate supporting device by means of which inflammation of the mucous membranes of the hard palate underneath the supporting device can be prevented by the patient, i.e. the wearer of the hard palate supporting device, himself.

This object is achieved according to the invention by a hard palate supporting device for distalizing or anchoring of upper teeth, such as molars and/or premolars, comprising:

a hard palate supporting element and/or carrier therefor;

hinge means by means of which said supporting element or said carrier is rotatable relative to an axis of rotation extending in the transverse direction of the teeth; and tensioning means which on rotation of said supporting element or said carrier in a direction away from the position resting against the hard palate exert on said supporting element or said carrier a force counteracting said rotation.

As a result of the hinged fastening of the supporting element, when the hard palate supporting device is fitted in the mouth the patient can press the supporting element downwards against the action of the tensioning means and thus clean the supporting element—or at any rate the contact face with which it rests against the hard palate—and the hard palate underneath the supporting element. This cleaning can be carried out using simple means, for example using a conventional or possibly adapted toothbrush, water jet means, etc. Inflammation of the underlying mucous membranes of the hard palate can be largely prevented by cleaning the supporting element and the part of the hard palate beneath it like this regularly, for example daily or several times a day, or once every few days, and oral hygiene is also improved considerably even when the hard palate supporting device is worn for a long time. The patient does not have to visit the orthodontist for such cleaning either.

In order to ensure that the supporting device cannot press too hard against the hard palate, thereby possibly causing the hard palate to deform and making wearing of the device unpleasant, or possibly adversely influencing the effect of the hard palate supporting device, it is advantageous according to the invention if the hard palate supporting device also comprises stop means which limit the rotation of the supporting element or the carrier to which said supporting element is fixed in the direction of the resting against the hard palate, the so-called contact direction. For optimum effect and optimum comfort during wear, said stop means will preferably limit the rotation in said contact direction to a contact position in which the supporting element just rests against the hard palate, or slightly beyond that. This ensures that the tensioning means as such have little or no effect on the hard palate.

In order to ensure that the supporting element is not turned away too far from the hard palate when the patient is carrying out the cleaning, or is not otherwise turned away too far from the hard palate, it is advantageous according to the invention if provision is also made for further stop means which limit the rotation of said supporting element or said carrier in the direction away from the contact position, or if the stop means for limiting the rotation in the contact direction also limit the rotation in the opposite direction. The supporting element here will preferably be rotatable through an angle range of 60° to 120°, for example approximately 90°. This also prevents the tensioning means from being excessively loaded and their service life thus being adversely affected.

According to an advantageous embodiment of the invention, the tensioning means comprise pretensioning means which in the contact position exert a pretensioning load which acts in the contact direction on said supporting element or said carrier. In this way it can be ensured that the supporting element rests sufficiently firmly against the hard palate, in order to prevent the effect of the supporting device according to the invention from being reduced as a result of the freedom of rotation.

When pretensioning means are used it is advantageous according to the invention if the pretensioning load is selected or designed in such a way that it substantially corresponds to the active reaction force desired or intended between the supporting element and hard palate for the distalizing or anchoring. In particular, if stop means are not used, or if the stop means limit the rotation beyond or just beyond the contact position, it is ensured in such a way that the supporting device according to the invention, as regards the play of forces active during use, is identical or virtually identical to similar supporting devices known from the prior art.

If the supporting device according to the invention is used with pretensioning means combined with stop means, it is advantageous according to the invention if the pretensioning load is selected or designed in such a way that said load is greater, preferably a multiple greater, than the active reaction force desired or intended between the supporting element and the hard palate for the distalizing or anchoring. The active reaction force between the supporting element and the hard palate is generally relatively small, so that the pretensioning load of the order of magnitude of a multiple of said desired or intended reaction force can easily be overcome by the patient, in order to free the supporting element from the hard palate by rotation thereof, for cleaning purposes. Selecting the pretensioning load in such a way that it is greater, preferably a multiple greater, also ensures that the desired and/or intended reaction force or reaction forces between the supporting element and the hard palate known from the prior art are not changed. A multiple here should be understood as meaning, for example, a factor of 1.5 to 5 times the so-called desired or intended reaction force, such as, for example, 2, 3, 4 or 5 times the desired or intended reaction force. Multiples with a greater value, for example ten times or fifteen times, are also conceivable, just provided that the patient can turn the supporting element away from the hard palate against the pretensioning load, for cleaning purposes.

The hard palate supporting device according to the invention can be achieved in many different ways. For example, it is conceivable for the carrier for the supporting element to be designed in such a way that it comprises two wire parts embedded in the supporting element and each extending from the supporting element to an opposite upper tooth to which said wire parts are to be fixed, that fixing being such that it allows the wire parts to hinge directly relative to the fixing means by means of which the wire parts are fixed to the tooth. This therefore means, as it were, two hinges situated on opposite sides of the set of teeth at the inside of the teeth, which hinges for a good hinging action will have their axes of rotation situated in line with each other. This is not so easy to achieve in practice, and such hinges are not very practical, since at the position where they are fixed to the tooth little space is generally available and solder is also often used, which could pass into the hinge and thus impede the hinging process.

The hard palate supporting device according to the invention can be achieved in an advantageous manner if the hinge means comprise a bush fixed to the supporting element or the carrier therefor and a wire which extends through said bush and is shape-retaining per se, and around which the bush can rotate, the ends of the wire being connectable by way of fixing means, such as premolar or molar bands, to upper teeth situated on either side of the set. The wire, or at any rate the part thereof extending through the bush, in this case forms the hinge pin of the hinge means and, as commonly occurs per se in orthodontics, the parts of the wire extending beyond the bush can be adapted relatively easily to the shape of the mouth, in particular the roof of the mouth, of the patient and can be fixed to fixing means which are common per se for fixing to teeth. In an advantageous manner, the wire, or at any rate the parts thereof situated beyond the bush, will be deformable, in such a way that the wire can assume a substantially U-shape, the underside of which U-shape faces the palate, and the legs of which U-shape extend from the underside of the U-shape to said teeth situated on either side of the set.

In the case of such an embodiment the tensioning means can advantageously comprise a torsion spring which acts upon the bush at one side and upon the wire at the other side. Such a torsion spring can be fitted around the wire, in which case said torsion spring forms an element in the mouth which is hardly noticed by the patient. Springs fitted or wound around a wire element are known per se in orthodontics and generally do not inconvenience the patient.

In order to increase the reliability of the effect, it is advantageous according to the invention in this case if the torsion spring is accommodated in the bush and around the wire. In this way the torsion spring is shielded from the environment by the bush.

In the case of the embodiment with a wire, the stop means in a hard palate supporting device according to the invention can advantageously comprise at least one stop element fitted on the wire. Such a stop element can comprise, for example, a bracket soldered or fixed in another way on the wire, on which bracket the carrier of the supporting element can rest in the contact position. But according to an advantageous embodiment it is also conceivable for the bush to be provided with at least one stop support acting with the at least one stop element. The stop element fixed to the wire then interacts with a stop support formed on or in the bush, in which case projecting parts, or at any rate parts which project far, can be avoided.

According to an advantageous embodiment, the stop element comprises a cylindrical element fixed on the wire, the external diameter of which element corresponds to that of the bush, and the cylindrical element at the end face thereof facing the bush is provided with a recess, into which a projection formed on the adjacent end face of the bush projects (or, conversely, the cylindrical element is provided with a projection which projects into a recess formed on the adjacent end face of the bush), in such a way that the rotation of the bush, and thus also of the carrier and the supporting element fixed or fixable thereto, is limited in two directions. The cylindrical element and the bush in this case are situated substantially in line with each other and next to each other in such a way that they connect up to each other. If desired, provision can also be made for the recess formed in the bush or in the cylindrical element to be such that in the circumferential direction of the cylindrical element or the bush it is closed or shut off/can be shut off by a covering element. This ensures that, for example, a part of the tongue cannot become caught in these stop means during rotation of the supporting element relative to the axis of rotation.

The supporting element in the case of the hard palate supporting device according to the invention can per se be any supporting element known from Nance appliance technology, and in general will be made of a plastic such as an acrylate or synthetic resin and adapted to the shape of the hard palate, at any rate as regards the contact face of the supporting element.

The present invention also relates to a method for making a hard palate supporting device according to the invention ready for fitting, in particular a hard palate supporting device according to the embodiment with a so-called wire, where the wire is bent, on the basis of a model of the upper teeth of a patient, to such a U-shape adapted to the contour of the roof of the mouth of the patient that the part of the wire with the bush is situated in the bottom part of the U and near, but at a contact-avoiding distance from the surface of the roof of the mouth, and that the legs of the U extend from here along, but at a contact-avoiding distance from the side walls of the roof of the mouth, to the teeth to which the wire is to be fixed. In such a way the hard palate supporting device according to the invention can be accommodated in the mouth in such a manner that the supporting device according to the invention projects as little as possible into the hollow formed between the upper jaws and runs as close as possible along the walls of the roof of the mouth without making contact therewith, thus increasing comfort during wear.

The carrier for the supporting element in this case can advantageously be made of a plastic, the carrier, or at least a part thereof, preferably being embedded in the supporting element.

According to a further advantageous embodiment, the ends of the wire can be soldered, welded or otherwise fastened to the fixing means, such as bands fitted around the teeth in question, or at any rate impressions thereof in the model of the upper teeth. Remaining surplus lengths of wire can be removed by adjusting the wire ends to size prior to or after soldering, welding or otherwise fastening them to the fixing means, by cutting or snipping off or otherwise severing the surplus parts.

During the adjustment of the supporting device according to the invention to size it is particularly advantageous if during the bending of the wire and/or fastening of the wire to the fixing means the procedure is such that the supporting element or the carrier therefor is situated substantially in the contact position, preferably resting against the stop.

In order to give the supporting device according to the invention an even more accurate fit, it is advantageous according to the invention if, after bending of the wire, fixing it to the fixing means and forming the supporting element, the wire and/or the carrier of the supporting element and/or the stop means are further bent until, in the position fitted in the model, in the contact position of the supporting element, a certain desired pressure load of the supporting element on the hard palate has been reached. When a stop is used, this certain desired pressure load will preferably be a zero load, in other words the contact position coincides with the stop position, so that the tensioning or pretensioning means exert no direct pressure on the hard palate.

BRIEF DESCRIPTION OF PREFERRED EMBODIMENT

The present invention will now be explained in greater detail with reference to exemplary embodiments shown diagrammatically in the drawing. In this drawing.

DESCRIPTION OF THE PREFERRED EMBODIMENT

Figure 1:
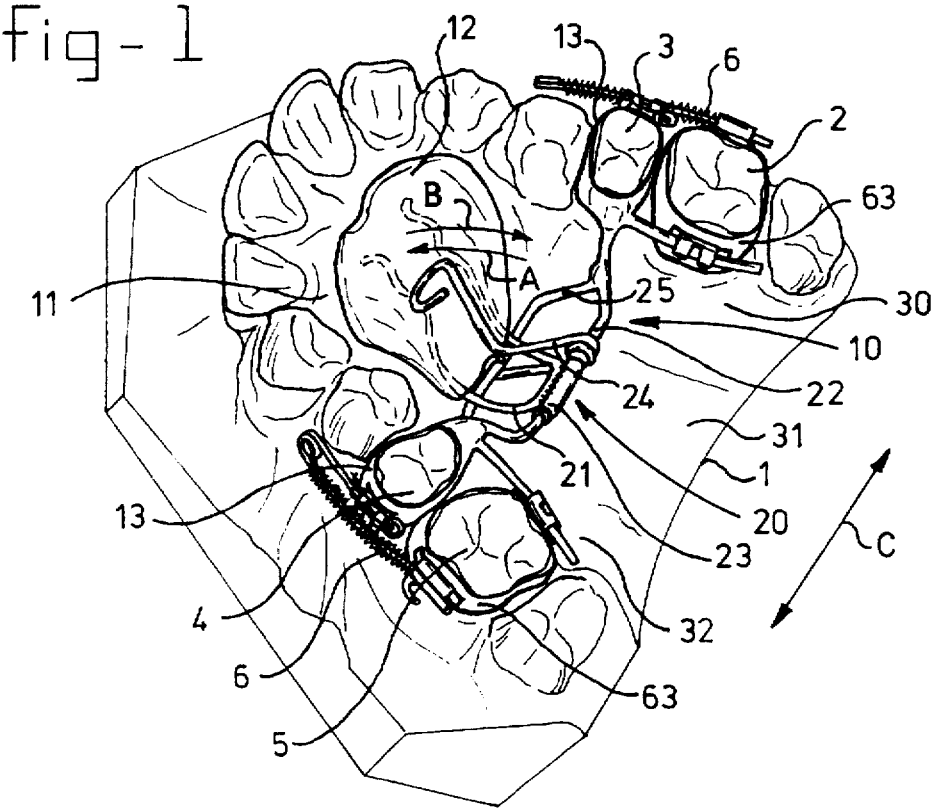
FIG. 1 shows in perspective a view of a model of the upper teeth of a patient, in which an exemplary embodiment of a hard palate supporting device according to the invention is fitted.

FIG. 1 shows a perspective view of a model 1 of the upper teeth of a patient, obtained by way of an impression. As can be seen, so-called premolar bands 13 and molar bands 63 are fitted around the molars 2 and 5 and around the premolars 3 and 4 respectively, and tensioning devices 6 (which can also be fixed on the inside of the (pre)molar bands) are provided on the outside of the (pre)molar bands 13, 63, in order to force the molar 2 and premolar 3 and the molar 5 and premolar 4 apart, for the purpose of a corrective orthodontic treatment. In order to ensure that such forcing apart occurs in a controlled manner here, it is important in each case that one of the teeth which is to be forced apart should be fixed further on either side of the set. For this purpose, the premolars 3 and 4 are supported against the hard palate 11 by means of a so-called Nance appliance or hard palate supporting device 10. As is usual per se, such a hard palate supporting device comprises a supporting element 12 made of plastic, of which the surface facing the hard palate is adapted in shape to the hard palate of the patient concerned. This is relatively simple to achieve by making this supporting element 12 of a material which in the plastic state can be shaped directly to the model of the teeth. The hard palate supporting device ensures that a reaction force is produced between the premolars 3 and 4 and the hard palate, in order to hold the premolars 3 and 4 in place while the molars 2 and 5 are being pushed away from them.

By means of, for example, a soldered connection, the supporting element is then firmly connected by way of a connecting system to the bands 13 around the premolars 3 and 4. However, it will be clear that the supporting element can also be connected by way of the connecting system to the bands 63 around the molars 2 and 5. The place of fixing will generally depend on the orthodontic treatment. The connecting system according to the invention comprises hinge means 20, by means of which the supporting element 12 is rotatable about an axis of rotation extending in the transverse direction of the teeth. The hinge means 12 here comprise a wire 22 surrounded by a bush 23, which can rotate relative to the wire 22. A carrier 21 is also soldered onto the bush 23, which carrier at the other side is embedded in the supporting element 12. A bracket 25 which, on the one hand, serves as a stop element and, on the other hand, serves as an action point (to prevent rotation around wire 22) of a resilient spring wire 24 which is wound around wire 22 and under spring tension presses against supporting element 12, is also soldered onto the wire 22. The rotation of the supporting element 12 in the pressure direction, in other words in the direction of the contact position (in which the supporting element 12 rests against the hard palate) is limited here by the fact that the bearing arm 21 is formed in such a way that in the contact position it rests against the stop bracket 25. If desired, instead thereof or in addition thereto, the spring 24 can also be formed in such a way that in the contact position it comes to a stop against the stop bracket 25.

Figure 2:
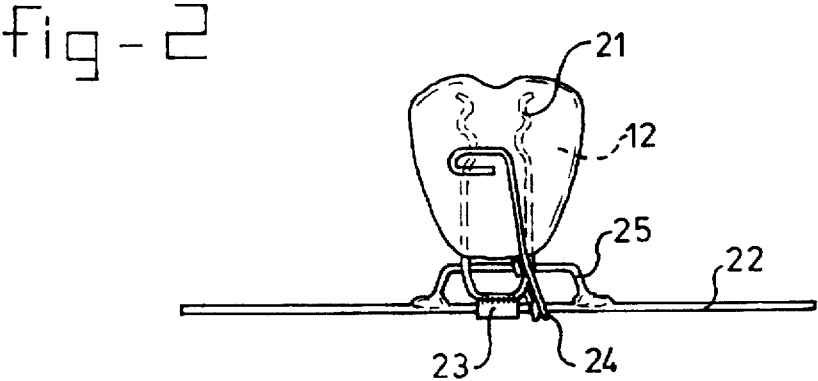
FIG. 2 shows a hard palate supporting device according to the invention, as used in the exemplary embodiment according to FIG. 1, but now in a position essentially prior to the hard palate supporting device being adjusted to size for a patient.

FIG. 2 shows the hard palate supporting device according to the invention prior to the fitted state adapted to the shape of the patient's upper teeth and the roof of the patient's mouth. The supporting element 12 is shown diagrammatically here in dashed lines, and not yet fitted. It will be clear that the invention also extends to such a hard palate supporting device in which the supporting element generally adjusted to size by the dental technician has not yet been fitted. The hard palate supporting device, as shown in FIG. 2, as yet without its supporting element, can be sold as a prefabricated part and delivered to the dental technician for adjusting to size.

As can be seen in FIG. 1, the wire 22 is adjusted to size and bent into a U-shape, said wire 22 then extending in the U-shape closely along the side walls 30, 32 of the roof of the mouth and the top surface 31 of the roof of the mouth. The closer the wire 22 runs along here, the less the patient will be aware of the hard palate supporting device, while for good comfort during wear it must be remembered that it is advantageous if the wire 22 and the construction parts formed thereon just stop short of making contact with the roof of the mouth. This can be achieved by fixing the wire 22 by its ends, as it were cantilevered (i.e. substantially free from contact with parts of the body other than teeth), to the premolar bands 13 and/or molar bands 63.

Figure 3:
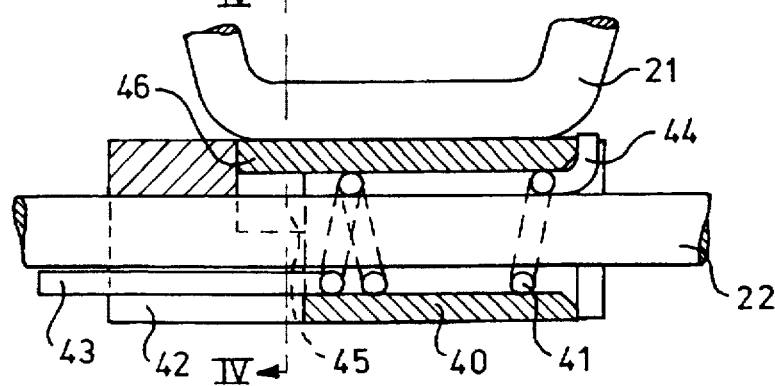
FIG. 3 shows a longitudinal section view, partially an elevational view of a hinge/pretensioning device, of a further exemplary embodiment of a hard palate supporting device according to the invention.
Figure 4:
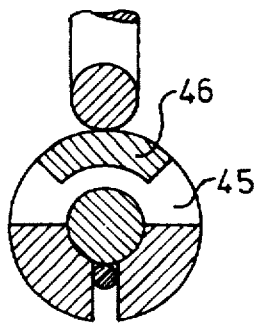
FIG. 4 shows a cross-section view according to the arrows IV—IV from FIG. 3.

FIGS. 3 and 4 show in greater detail a preferred embodiment of a hard palate supporting device according to the invention, or at any rate the hinge means and pretensioning means thereof. The embodiment shown in FIGS. 3 and 4 corresponds largely to that of FIGS. 1 and 2, except that the stop bracket 25 is absent, the spring 24 has been omitted and is replaced by other pretensioning means, and the bush 23 has been modified slightly in design. For the rest, the embodiment according to FIGS. 3 and 4 corresponds substantially to that according to FIGS. 1 and 2. For that reason, corresponding, essentially identical parts are indicated by the same reference symbols, in other words, the carrier 21 and the wire 22. The carrier 21 is firmly fixed to a bush 40 which is fitted around the wire 22 and in which a torsion spring 41 is accommodated. A cylindrical element 42, firmly connected to the wire 22, is provided alongside and connecting to the bush 40. The cylindrical element 42 is provided with a longitudinal passage through which one end 43 of the torsion spring 41 projects, in order to fix said end 43 of the torsion spring 41 relative to the cylindrical element 42, and thus also relative to the wire 22. The other end 44 of the torsion spring 41 is fixed to the bush 40, by folding said end 44 over and dropping it into a recess formed in the bush 40. It will be clear that the torsion spring 41 can be pretensioned, in order to exert a pretensioning load on the carrier 21 in the so-called contact direction.

The stop means in the embodiment according to FIGS. 3 and 4 are obtained by providing the cylindrical element 42 with a semi-cylindrical cutout 45 which opens out at the end face facing the bush 40, and into which a projection 46 formed on the bush 40 projects, which projection 46 extends here over approximately a quarter of a circle. This means that the carrier 21 and the supporting element possibly fixed thereto can rotate through a range of 90° between a contact position and a position rotated through 90° from the contact position 30. In one case the projection 46 will come to rest with its one longitudinal side against the cylindrical element 42, and in the other case will do so with its other longitudinal side.

As will be clear, the patient can lift the supporting element of a supporting device according to the invention off the roof of the mouth by rotating it in the direction of arrow A about the axis of rotation. The patient can then clean the roof of the mouth and the contact face of the supporting element himself, after which, when the supporting element has been released, the tensioning means, ensure a rotation in the direction of arrow B, in order to make the supporting element rest against the roof of the mouth again.

The hard palate supporting device according to the invention can be fixed to teeth in many different ways. Instead of (pre)molar bands 16, 63, so-called brackets, for example to be bonded to one or more teeth, can also be used.

The carrier 21, wire 22, part 25, the spring, the hinge etc. can be made of any suitable material. For example, metals/alloys of the type commonly used in the mouth in orthodontics can be used.

I claim:

1. A hard palate supporting device for orthodontic treatment of upper teeth, comprising:
    a carrier for carrying a hard palate supporting element;
    hinge means for rotating said carrier about an axis of rotation extending transversely to said carrier; and
    tensioning means for urging rotation of said carrier in a first direction toward a position of a hard palate when the supporting device is installed for orthodontic treatment of upper teeth.

2. The device of claim 1, further comprising stop means for limiting rotation of said carrier.

3. The device of claim 2, wherein said stop means limits rotation of said carrier in the first direction to a first position which corresponds to the hard palate when the supporting device is installed for orthodontic treatment of upper teeth.

4. The device of claim 3, wherein said stop means limits rotation to at least 60° to no more than 120° from the first position in a second direction opposite the first direction.

5. The device of claim 3, wherein said tensioning means urges said carrier with a force that is greater than an active reaction force for the orthodontic treatment when said carrier is in the first position and the supporting device is installed for orthodontic treatment of upper teeth.

6. The device of claim 2, wherein rotation of said carrier is limited to a range of at least 60° to no more than 120°.

7. The device of claim 1, wherein said tensioning means urges said carrier with a force that corresponds to an active reaction force for the orthodontic treatment when the supporting device is installed for orthodontic treatment of upper teeth.

8. The device of claim 1, further comprising a shape-retaining wire that is the axis of rotation of said hinge means and that has ends that are arranged and constructed to be connected to teeth on opposite sides of a mouth when the supporting device is installed for orthodontic treatment of upper teeth, and wherein said hinge means comprises a bush attached to said carrier and that rotates about said wire.

9. The device of claim 8, wherein said wire has an U-shape and said bush is positioned at a center portion thereof.

10. The device of claim 8, wherein said tensioning means comprises a torsion spring for applying a force between said bush and said wire.

11. The device of claim 10, wherein said torsion spring is inside said bush and around said wire.

12. The device of claim 8, wherein said wire comprises a stop element fitted thereon for limiting rotation of said carrier in the first direction to a first position which corresponds to the hard palate when the supporting device is installed for orthodontic treatment of upper teeth.

13. The device of claim 12, wherein said bush comprises a stop support for interacting with said stop element.

14. The device of claim 12, wherein said stop element comprises a cylindrical element fixed on said wire, the external diameter of which corresponds to an external diameter of said bush, and in which one of said cylindrical element and said bush has a recess at an end face thereof and wherein the other of said bush and said cylindrical element comprises a projection that projects into said recess.

15. The device of claim 1, further comprising the hard palate supporting element, and wherein said hard palate supporting element comprises plastic arranged and constructed to correspond to a shape of the hard palate.

16. A method of making a hard palate supporting device for orthodontic treatment of upper teeth, comprising the steps of:
    providing a carrier for carrying a hard palate supporting element, the carrier being attached to a bush that rotates about a wire which extends transverse to the carrier so that the carrier rotates about a middle portion of the wire;
    bending the wire on the basis of a model of the upper teeth in an U-shape to conform to a shape of a hard palate part of the model;
    connecting tensioning means to the bush and the wire to urge rotation of the carrier in a first direction toward a position of a hard palate when the supporting device is installed for orthodontic treatment of upper teeth.

17. The method of claim 16, wherein the wire is bent so that the bush avoids contact with the hard palate and so that legs of the wire extending from both sides of the bush avoid contact with the mouth, when the supporting device is installed for orthodontic treatment of upper teeth.

18. The method of claim 16, further comprising the step of embedding the carrier in the hard palate supporting element that is made of plastic.

19. The method of claim 16, further comprising the step of affixing ends of the wire to bands fitted to the teeth.

20. The method of claim 19, wherein when the ends of the wire are being affixed to the bands, the carrier is in the position of the hard palate.

21. The method of claim 16, further comprising the step of bending one of the wire and the carrier so that when the carrier is in the position of the hard palate when the supporting device is installed for orthodontic treatment of upper teeth a desired load of the supporting element on the hard palate is achieved.

* * * * *